(12) United States Patent
Kuo et al.

(10) Patent No.: US 7,759,487 B2
(45) Date of Patent: Jul. 20, 2010

(54) PREPARATION OF KETONE AMIDES

(75) Inventors: Shen-Chun Kuo, Union, NJ (US);
David Jieh-Shyh Tsai, Warren, NJ (US);
Hongbiao Liao, Bridgewater, NJ (US)

(73) Assignee: Schering Corporation, Kenilworth, NJ (US)

( * ) Notice: Subject to any disclaimer, the term of this patent is extended or adjusted under 35 U.S.C. 154(b) by 217 days.

(21) Appl. No.: 11/326,156

(22) Filed: Jan. 5, 2006

(65) Prior Publication Data

US 2006/0247437 A1 Nov. 2, 2006

Related U.S. Application Data

(60) Provisional application No. 60/641,899, filed on Jan. 6, 2005.

(51) Int. Cl.
*C07D 239/04* (2006.01)
(52) U.S. Cl. .................. 544/335; 546/193; 546/221
(58) Field of Classification Search ............... 544/333, 544/335; 546/193, 221
See application file for complete search history.

(56) References Cited

U.S. PATENT DOCUMENTS

| 6,602,885 | B2 | | 8/2003 | Baroudy et al. |
| 6,689,765 | B2 | | 2/2004 | Baroudy et al. |
| 6,992,189 | B2 | * | 1/2006 | Leong et al. ............ 544/295 |

FOREIGN PATENT DOCUMENTS

| WO | WO 03/035654 | * | 5/2003 |
| WO | WO03/084950 | | 10/2003 |

OTHER PUBLICATIONS

Wirth, Salmon, and Jones, Encyclopedia of Reagents for Organic Synthesis, 2001, John Wiley & Son, Ltd.*
Zhihua et al., Synthesis, Aug. 1993, 803-808.*
Manetti et al., Bioorganic and Medicinal Chemistry Letters, 13, 2003, 2303-2306.*
Bull, Henry B., "An Introduction to Physical Biochemistry", F.A. Davis Co, 1964.*
International Search Report, PCT/US2006/000251; mailed Jun. 20, 2006; 5 pages.
Xu, G.; et. al.; "Synthesis of Substituted Diarylmethylenepiperidines (DAMPs), a Novel Class of Anti-HIV Agents", Bioorganic & Medicinal Chemistry; vol. 10, 2002; pp. 2807-2816.

* cited by examiner

*Primary Examiner*—Bernard Dentz
*Assistant Examiner*—David E Gallis
(74) *Attorney, Agent, or Firm*—Patent Practitioners of Schering Corporation

(57) ABSTRACT

The present invention discloses a novel process to prepare ketone amides, which are useful intermediates for the preparation of antagonists of CCR5 receptor and therefore useful for the treatment of HIV virus infected mammals. It specifically discloses a novel process to synthesize 1-(2,4-dimethylpyrimidine-5-carbonyl)-4-piperidone, 1-[(2,4-dimethyl-3-pyridinyl)carbonyl]-4-piperidone and related compounds. A salient feature of the invention is the use of a three-phase reaction medium with an organic phase and a buffer salt slurry.

8 Claims, No Drawings

PREPARATION OF KETONE AMIDES

CROSS REFERENCE TO PRIORITY APPLICATION

This application claims the benefit of priority to U.S. provisional application Ser. No. 60/641,899 filed Jan. 6, 2005.

FIELD OF THE INVENTION

This patent application discloses a novel process to prepare ketone amides, which are useful intermediates for the preparation of antagonists of CCR5 receptor useful for the treatment of HIV virus infected mammals. This application includes a novel process to synthesize 1-(2,4-dimethyl-pyrimidine-5-carbonyl)-4-piperidone, 1-[(2,4-dimethyl-3-pyridinyl)carbonyl]-4-piperidone and related compounds.

BACKGROUND OF THE INVENTION

U.S. Pat. Nos. 6,602,885; 6,387,930; 6,689,765; and 6,391,865, all to Schering-Plough Corporation, disclose several novel antagonists of the CCR5 receptor which are useful for the treatment of AIDS and related HIV infections. Particular reference is made to the compounds of formulas I and II:

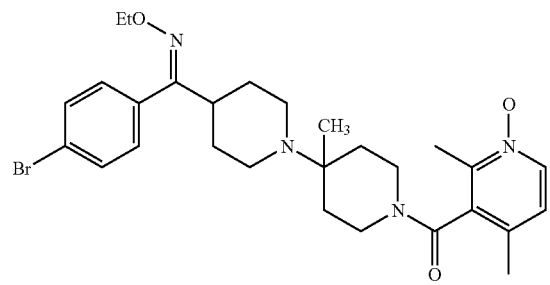

as disclosed in U.S. Pat. Nos. 6,602,885 and 6,387,930.

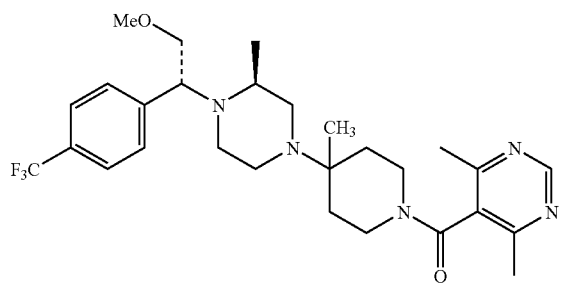

as disclosed in U.S. Pat. Nos. 6,689,765 and 6,391,865.

CCR-5 receptors have also been reported to mediate cell transfer in inflammatory diseases such as arthritis, rheumatoid arthritis, atopic dermatitis, psoriasis, asthma and allergies, and inhibitors of such receptors are expected to be useful in the treatment of such diseases, and in the treatment of other inflammatory diseases or conditions such as inflammatory bowel disease, multiple sclerosis, solid organ transplant rejection and graft v. host disease.

In view of the importance of antagonists of the CCR5 receptor, new, novel methods of making such antagonists are always of interest.

SUMMARY OF THE INVENTION

There is provided in accordance with the present invention a process for preparing a ketone amide of formula 5' from an acid chloride:

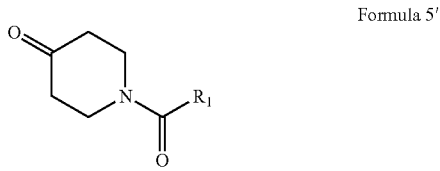

Formula 5' where $R_1$ is a substituent selected from alkyl, aryl, cycloalkyl, heteroaryl and heterocyclyl moieties, with the proviso that $R_1$ does not contain a primary or secondary amine. The said alkyl, aryl, cycloalkyl, heteroaryl and heterocyclyl moieties may optionally be substituted with the proviso that the substituents do not contain a primary or secondary amine.

A salient feature of this inventive procedure is that while acid chlorides are reactive to water so that aqueous reaction media cannot be used when using an acid chloride as a reagent, the current process employs a multiphase reaction/reagent medium with a heavily salted aqueous phase and a distinct organic phase, allowing the reaction to proceed with high yields without hydrolyzing the acid chloride. Not intending to be bound by any theory, it is believed that the acid chloride dissolves in acetonitrile, for example, which remains as a distinct phase from a concentrated aqueous salt phase. Particularly useful in connection with the process is where the concentrated aqueous salt phase comprises a phosphate salt buffer system.

The presence of the phosphate buffer reduces the solubility of the highly water soluble product ketone amide (5') in the aqueous phase, which results in efficient separation of the final product ketone amide, avoiding multiple additional purification steps.

The buffer also reduces unwanted by-product (e.g. see compound 6 below) by controlling the pH.

The novel process per se is to prepare ketone amides, which, in turn, are useful intermediates for the preparation of several compounds. Of particular interest is their use for the preparation of antagonists of CCR5 receptor (Formulas I and II above).

DESCRIPTION OF THE INVENTION

Except where stated otherwise, terminology is given its ordinary meaning as is set forth in the following exemplary definitions. Chemical names, common names, and chemical structures may be used interchangeably to describe the same structure. These definitions apply regardless of whether a term is used by itself or in combination with other terms, unless otherwise indicated.

"Alkyl" means an aliphatic hydrocarbon group which may be straight or branched and typically includes from about 1 to about 20 carbon atoms in the chain. Suitable alkyl groups contain about 1 to about 12 carbon atoms in the chain such as from about 1 to about 6 carbon atoms in the chain and include both branched alkyl and lower alkyl. Branched alkyl means that one or more lower alkyl groups such as methyl, ethyl or propyl, are attached to a linear alkyl chain. "Lower alkyl" means a group having about 1 to about 6 carbon atoms in the chain which may be straight or branched. The alkyl group may be substituted by one or more substituents which may be the same or different, and may include heteroatoms.

"Aryl" (sometimes abbreviated "Ar") means an aromatic monocyclic or multicyclic ring system comprising about 6 to about 14 carbon atoms, preferably about 6 to about 10 carbon atoms. The aryl group can be optionally substituted with one or more ring system substituents which may be the same or different. Non-limiting examples of suitable aryl groups include phenyl and naphthyl.

"Cycloalkyl" means a non-aromatic mono- or multicyclic ring system comprising about 3 to about 10 carbon atoms, preferably about 5 to about 10 carbon atoms. Suitable cycloalkyl rings contain about 5 to about 7 ring atoms. The cycloalkyl can be optionally substituted with one or more ring system substituents which may be the same or different. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Suitable heteroaryls contain about 5 to about 6 ring atoms. The "heteroaryl" may be substituted by one or more ring system substituents which may be the same or different. Non-limiting examples of suitable heteroaryls include pyridinyl and pyrimidinyl.

"Heterocyclyl" (or heterocycloalkyl) means a non-aromatic monocyclic or multicyclic ring system comprising about 3 to about 10 ring atoms, suitably with from about 5 to about 10 ring atoms, in which one or more of the atoms in the ring system is an element other than carbon, for example nitrogen, oxygen or sulfur, alone or in combination. These rings are also optionally substituted.

Suitable substituents for the above-noted alkyl, aryl, cycloalkyl, heteroaryl and heterocyclyl moieties may be the same or different, each substituent being independently selected from the group consisting of halo, alkyl, aryl, cycloalkyl, cyano, alkoxy, alkylthio, ketone, —C(O)O-alkyl and the like.

A "concentrated" aqueous salt means a salt/water solution containing at least about 50 percent of the salt present in a corresponding saturated solution of salt. Aqueous salt slurries have a saturated aqueous component as well as a solid salt phase.

There is provided in a first aspect of the invention a process for preparing a ketone amide of formula 5':

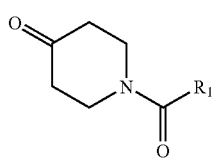

Formula 5' where $R_1$ is a substituent selected from alkyl, aryl, cycloalkyl, heteroaryl and heterocyclyl substituents, with the proviso that $R_1$ does not contain a primary or secondary amine, the process comprising: (i) reacting a carboxylic acid of formula 1:

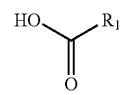

Formula 1 with a chlorinating reagent for substituting a chlorine atom for a hydroxy radical in the carboxylic acid (i.e., a reagent that forms an acid chloride from a carboxylic acid), utilizing a catalyst and a non-protic solvent to produce a solution of the acid chloride of formula 2:

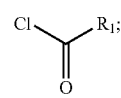

Formula 2

(ii) separately preparing a multiphase reaction medium with a concentrated aqueous salt phase and an organic phase comprising a suitable non-protic solvent, the medium also being provided with a compound of formula 3:

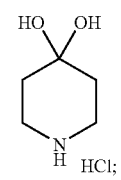

Formula 3 and adding the solution of the acid chloride to reaction medium to yield the ketone amide of formula 5':

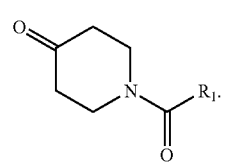

Formula 5'

In one embodiment $R_1$ is:

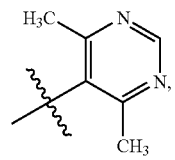

and in another $R_1$ is:

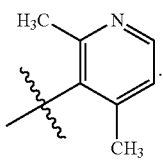

The chlorinating reagent in step (i) may be oxalyl chloride, thionyl chloride or phosphoryl chloride, while the catalyst in step (i) is dimethyl formamide (DMF). The non-protic solvent in steps (i) and (ii) is separately and independently selected from the group consisting of acetonitrile, propionitrile, benzene, toluene, xylene, chlorobenzene, dichloro-benzene, $C_5$-$C_{12}$ ether, 1,2-dimethoxyethane, 1.2-diethoxyethane, diglyme, 1,4-dioxane, tetrahydrofuran, $C_1$-$C_5$ ester and said chlorinating reagent and appropriate mixtures thereof. The temperature of the reaction in step (i) ranges generally from −20 to 60° C., preferably from −10 to 20° C., more preferably from −5 to 5° C.

The multiphase reaction medium is a three phase reaction system comprising an aqueous salt slurry and a non-protic solvent in particularly advantageous applications of the invention. Another embodiment is where the concentrated aqueous salt phase comprises a buffer system with $K_3PO_4$ and $K_2HPO_4$, such as wherein the $K_3PO_4$ and $K_2HPO_4$ are present in a ratio ranging from 2.5:0.5 to 0.5:2.5 or wherein said $K_3PO_4$ and $K_2HPO_4$ are present in a ratio of 1:2. The buffer system in step (ii) may maintain the pH in the range of 7.5-9.5, or may maintain the pH in the range of 8.0-9.0.

The temperature of said reaction in step (ii) ranges generally from −15 to 60° C. in most cases, such as from −10 to 20° C. or from −5 to 10° C.

Another aspect of the invention is a process for the preparation of the compound of formula 5 from a solution of an acid chloride of formula 2', said process comprising adding a solution of the acid chloride of formula 2' to a multiphase reaction medium containing a compound of formula 3, which reaction medium contains a concentrated aqueous salt phase and an organic phase comprising a suitable non-protic solvent, to produce the compound of formula 5, in accordance with the following equation:

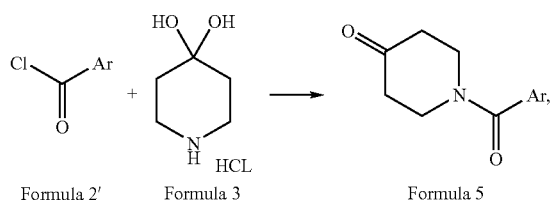

where Ar is

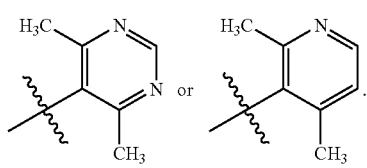

The present invention resides, in part, in the discovery that, while normally an acid chloride is water reactive and so aqueous reaction media cannot be used when using an acid chloride as a reagent, it is possible to use a multiphase reaction/reagent medium with a heavily salted aqueous phase without hydrolyzing the acid chloride.

The phosphate buffer, used in accordance with this invention, maintains a constant pH of 8-9 throughout the reaction, which reduces formation of the side product (6). The phosphate buffer, by virtue of its good water solubility, reduces the solubility of the ketone amine thus improving the efficiency of isolation by eliminating multiple organic extractions. These improvements result in a highly efficient process that produces a high purity final product.

The inventive process is schematically described in the Scheme below:

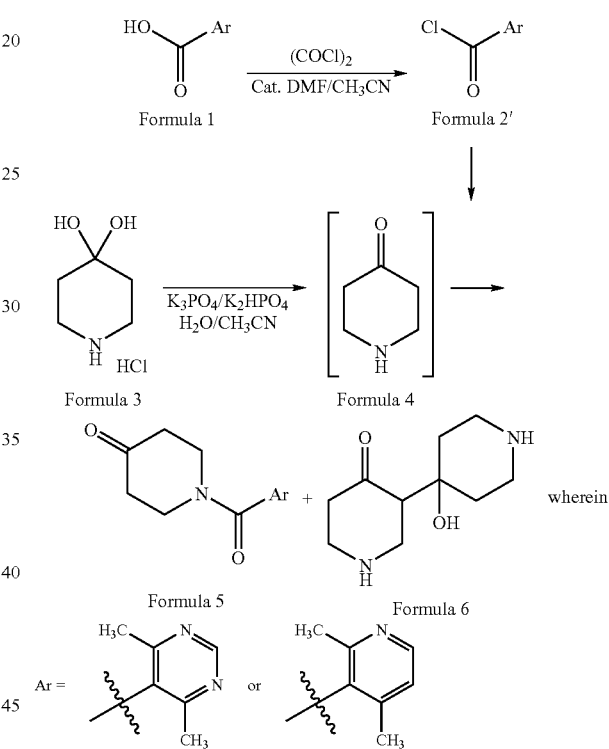

The compound of Formula 5 can be further converted to the CCR5 antagonist compounds of Formula I and Formula II if so desired.

The following nonlimiting EXAMPLES are provided in order to further illustrate the present invention.

EXAMPLES

Unless otherwise stated, the following abbreviations have the stated meanings in the Examples and Table 1 below:
$CDCl_3$=Deuterochloroform
$CH_3CN$=Acetonitrile
DMF=Dimethylformamide
g=grams
$K_2HPO_4$=Potassium hydrogen phosphate
$K_3PO_4$=Potassium phosphate
mL=milliliters MS=Mass spectrum
NMR=Nuclear magnetic resonance spectroscopy

EXAMPLES

Example 1

Preparation of 1-(2,4-dimethylpyrimidine-5-carbonyl)-4-piperidone—Compound IV

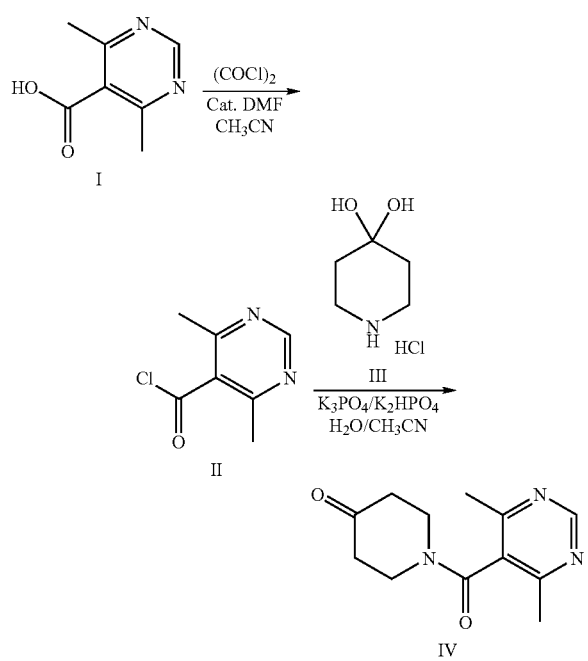

To a suspension solution of 90.0 g of 4,6-dimethylpyrimidine-5-carboxylic acid (I) and a catalytic amount of dimethylformamide (0.45 mL) in $CH_3CN$ (630 mL) was slowly added oxalyl chloride (78.8 g) at −5° C. to 5° C. The reaction was then aged at 0° C. for 2 hours.

In a separate flask, a heterogeneous mixture of $K_3PO_4$ (136.1 g), $K_2HPO_4$ (205.9 g) in water (270 mL) and $CH_3CN$ (540 mL) at 0° C. was added to a solution of 99.8 g of 4-piperidone monohydrate hydrochloride (III) in water (135 mL). The reaction mixture was agitated at 0° C. for 2 hours.

The 4,6-dimethylpyrimidine-5-carboxyl chloride (II) solution was transferred to the buffered piperidone solution slowly and the reaction temperature was maintained below 10° C. After the addition, the reaction mixture was agitated at 10° C. for 4 hours. Once the reaction is completed, charcoal (18.0 g) was added to lessen the color. The reaction mixture was filtered to remove the solid residue and the lower aqueous layer was then separated from the top $CH_3CN$ layer. The $CH_3CN$ solution was removed and replaced with ethyl acetate (1350 mL) by distillation. The ethyl acetate solution was washed with an aqueous solution of $K_2HPO_4$ (90.0 g) in water (180 mL). The ethyl acetate solution was concentrated to about 270 mL then heptane (630 mL) was added to effect the precipitation of product. The solid product was filtered and dried in a vacuum oven at a temperature of 55° C. for 16 hours to give a yellowish solid (114.7 g).

$^1$HNMR ($CDCl_3$, δ): 8.96 (s, 1H), 4.10 (t, 2H), 3.49 (t, 2H), 2.66 (t, 2H), 2.46 (s, 6H), 2.39 (t, 2H). MS: 234 (M+1), 135, 100, Melting point: 116° C.

Example 2

Preparation of 1-[(2,4-dimethyl-3-pyridinyl)carbonyl]-4-piperidone—Compound VII

To a suspension solution of 200 g of 2,4-dimethyl pyridinyl-3-carboxylic acid (V) and a catalytic amount of dimethylformamide (1.0 mL) in $CH_3CN$ (1000 mL) was added oxalyl chloride (142.6 g) slowly at 20° C. The reaction was aged at 20° C. for 2 hours.

In a separate three neck jacketed flask were charged $K_3PO_4$ (680 g), 180 g of 4-piperodone monohydrate hydrochloride (III) followed by $CH_3CN$ (1400 mL) and water (600 mL). The reaction mixture was agitated at 22° C. for 2 hours and then the 2,4-dimethyl pyridinyl-3-carboxyl chloride (VI) was added slowly and the batch temperature maintained below 30° C. The reaction mixture was agitated at 23° C. for 2 hours to complete the reaction. The bottom aqueous layer with solid residue was removed. The top organic layer was concentrated to dryness to give oily product (262.8 g). The oil solidified at standing for 2 days. The product is a mixture of 1/1 free ketone and hydrate.

$^1$HNMR ($CDCl_3$, δ): 8.17 (q, 1H), 7.09 (q, 1H), 3.95 (t, 1H), 3.71 (t, 1H), 3.49 (t, 1H), 3.20 (t, 1H), 2.60 (t, 1H), 2.38 (t, 1H), 2.32 (d, 3H), 2.20 (d, 3H), 1.90 (t, 1H), 1.58 (t, 1H). MS: 233 (M+1), 100. Melting point: 64° C.

While the EXAMPLES are described herein as the preparation of the compounds of Formula IV and VII, it will be apparent to those skilled in the art that many modifications, variations and alterations to the present disclosure, both to materials, methods and reaction conditions, may be practiced. All such modifications, variations and alterations are intended to be within the spirit and scope of the present invention.

What is claimed is:

1. A process for preparing a ketone amide of formula 5':

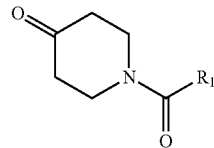

where $R_1$ is a substituent selected from alkyl, aryl, cycloalkyl, heteroaryl and heterocyclyl substituents, with the proviso that $R_1$ does not contain a primary or secondary amine, said process comprising:

(i) reacting in an acetonitrile reaction solvent a carboxylic acid of formula 1:

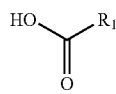

with a chlorinating reagent for substituting a chlorine atom for a hydroxy radical in the carboxylic acid, utilizing a catalyst and a non-protic solvent to produce a first solution of the acid chloride of formula 2:

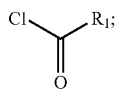

(ii) separately preparing a multiphase reaction medium with a concentrated aqueous salt phase comprising a buffer system with $K_3PO_4$ and $K_2HPO_4$ and an organic phase comprising acetonitrile solvent and the compound of formula 3:

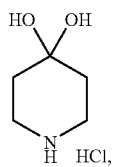

and adding said first solution of the acid chloride to said reaction medium to yield the ketone amide of formula 5':

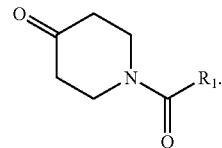

2. The process of claim 1, wherein said chlorinating reagent in step (i) is oxalyl chloride, thionyl chloride or phosphoryl chloride.

3. The process of claim 1, wherein said catalyst in step (i) is dimethyl formamide (DMF).

4. The process of claim 1, wherein said $K_3PO_4$ and $K_2HPO_4$ are present in a ratio ranging from 2.5:0.5 to 0.5:2.5.

5. The process of claim 4, wherein said $K_3PO_4$ and $K_2HPO_4$ are present in a ratio of 1:2.

6. The process of claim 2, wherein said chlorinating reagent is oxalyl chloride.

7. The process of claim 2, wherein said chlorinating reagent is thionyl chloride.

8. A process for the preparation of the compound of formula 5 from a solution of an acid chloride of formula 2', said process comprising adding a solution of the acid chloride of formula 2' to multiphase reaction medium containing a compound of formula 3, which reaction medium contains a concentrated aqueous salt phase and an organic phase comprising acetonitrile to produce the compound of formula 5, in accordance with the following equation:

where Ar is:

* * * * *